United States Patent [19]

Boyden

[11] 4,069,279
[45] Jan. 17, 1978

[54] DIALKYLPHENOL PHOSPHORYLATION

[75] Inventor: Julian William Boyden, Eastwood, England

[73] Assignee: Albright & Wilson Limited, Warley, England

[21] Appl. No.: 343,602

[22] Filed: Mar. 21, 1973

[30] Foreign Application Priority Data

Mar. 23, 1972 United Kingdom ............... 13668/72

[51] Int. Cl.$^2$ ............................................... C07F 9/12
[52] U.S. Cl. .................................... 260/975; 260/966; 260/973; 260/974; 260/976; 260/978; 260/980
[58] Field of Search ............... 260/966, 974, 975, 973, 260/976, 978, 980

[56] References Cited
U.S. PATENT DOCUMENTS

| 3,553,155 | 1/1971  | Garrett .......................... 260/966 X |
| 3,576,923 | 4/1971  | Randell et al. ...................... 260/966 |
| 3,780,145 | 12/1973 | Malec ................................. 260/966 |
| 3,801,683 | 4/1974  | Kodama et al. ................. 260/974 X |

Primary Examiner—Richard L. Raymond
Attorney, Agent, or Firm—Flynn & Frishauf

[57] ABSTRACT

A process of manufacturing triaryl phosphate mixtures which comprises:
1. reacting a phosphorylation agent with a recycle composition of phenols, optionally in the presence of an additional composition of phenols, the total molar proportion to atoms of phosphorus in the phosphorylating agent being less than 3:1;
2. reacting the product of stage (1) with a feedstock composition of phenols as hereinafter defined, the proportion of feedstock composition added at (2) being such that the total molar proportion of phenols fed into the process to phosphorus atoms is at least 3:1;
3. recovering unreacted phenols from the stage (2) product to form the aforesaid cycle composition of phenols; and
4. recycling said recycle composition to stage (1).

24 Claims, No Drawings

DIALKYLPHENOL PHOSPHORYLATION

This invention relates to a chemical process for the manufacture of triaryl phosphate mixtures.

It is known to manufacture triaryl phosphate mixtures for use as PVC plasticizers and functional fluid additives by reacting a mixture of phenols with a phosphorylating agent, normally phosphorus oxychloride, $POCl_3$. Both batch and continuous versions of this process are known and are used on an extensive and increasing scale in many countries for the manufacture of triaryl phosphate plasticizers. Such triaryl phosphate mixtures are to be distinguished from substantially homogeneous triaryl phosphates comprising two or three different aryl moieties such as may be prepared by the process described in U.S. Pat. No. 2,071,323. Homogeneous triaryl phosphates do not find any substantial commercial use. This invention is not concerned with alkyl/aryl phosphates which may be made by reacting a phosphorylating agent with alcohols and phenols e.g. as described in British Pat. No. 734,768.

Commercially used triaryl phosphate plasticisers are made from mixtures of phenol itself and alkyl phenols. Two types of alkyl phenol precursors can be distinguished; the so called 'coal tar' phenols, made by distillation of coal coking residues, and comprising predominantly cresols and xylenols on the one hand, and synthetic alkyl phenols made by Friedel-Crafts alkylation of phenol and consisting essentially of $C_3$ — and higher substituted phenols on the other. An example of a process of phosphorylating coal tar phenols is found in U.S. Pat. No. 2,870,192.

The commercial process hitherto used for the manufacture of triaryl phosphates from these synthetic alkyl phenols has the drawback that it produces substantial quantities of unusable phenolic by-products consisting essentially of a a proportion of the di- and poly-alkyl phenols which were present in the original synthetic alkyl phenol feedstock obtained by the Friedel-Crafts process. These materials represent the least reactive of those subjected to phosphorylation and tend to pass through the phosphorylation procedure unchanged. This represents, of course, a waste of raw material. However, even had it been possible previously to utilise these raw materials such a course would have been rejected by technologists for the manufacture of triaryl phosphate mixtures intended for use as PVC plasticizers since the by-product comprises a large proportion of 2,6-dialkylphenols which are known to be susceptible to degradation to coloured by-products which are objectionable in PVC.

It would be possible to remove these less reactive phenols from the initial phenolic precursors by preliminary fractionation, but such a procedure would be uneconomic. Consequently, it has hitherto been the practice of synthetic triaryl phosphate manufacturers to accumulate and discard considerable quantities of these materials.

We have now discovered a process of manufacturing 'synthetic' triaryl phosphates which substantially mitigates the aforesaid problems arising from the accumulation of unreactive phenolic by-products, brings about a significant increase in plant capacity and output and provides triaryl phosphates having excellent properties as PVC plasticizers and functional fluid additives.

The invention provides a process of manufacturing triaryl phosphate mixtures which comprises:

1. reacting a phosphorylating agent with a recycle composition of phenols, optionally in the presence of an additional composition of phenols, the total molar proportion of phenols to atoms of phosphorus in the phosphorylating agent being less than 3:1;

2. reacting the product of stage (1) with a feedstock composition of phenols as hereinafter defined the proportion of feedstock composition added at (2) being such that the total molar proportion of phenols fed into the process to phosphorus atoms is at least 3:1;

3. recovering unreacted phenols from the stage (2) product to form the aforesaid cycle composition of phenols; and 4. recycling said recycle composition to stage (1).

The feedstock composition of phenols is herein defined as a product obtained by alkylating phenol itself or a mixture of phenols comprising a major molar proportion of phenols having less than three alkyl carbon atoms with an alkylating agent containing from three to sixteen carbon atoms per molecule. Where mixtures of alkylphenols are used they will normally be those derived from coal tar such as the so called 'coal tar cresols' and 'coal tar xylenols' which consist of a spectrum of alkylphenols of various molecular weights including minor quantities, usually 5 to 15 moles percent of $C_3$ — or higher substituted alkylphenols.

Preferably, the phenol starting material for the feedstock mixture is phenol itself which may be derived from any source, such as the decomposition of cumene hydroperoxide, the sulphonation of benzene or the hydrolysis of monochlorbenzene. Preferably, the phenol is free of substantially free of alkylated phenols.

The alkylation leading to the second feedstock composition may be conducted conventionally, e.g. described in U.K. patent specification No. 1,146,173. Conveniently, the Friedel Crafts alkylation procedure may be used. Thus the alkylating agent may be an alkyl halide, an alcohol or an alkene. Useful alkyl halides included those with straight and branched chain alkyl groups, preferably containing from three to six carbon atoms, and cycloalkyl groups preferably containing from six to twelve carbon atoms. Useful alcohols include primary, secondary and tertiary alcohols preferably containing from three to six carbon atoms per molecule such as isopropanol, tert butyl or tert amyl alcohol and cyclohexanol. Alkylation may be advantageously carried out in the presence of a gaseous hydrogen halide such as hydrogen chloride.

Alkene alkylating agents are preferred. Desirably these comprise from three to six carbon atoms. Propylene and n-butylene are most preferred.

The feedstock composition of phenols will normally comprise both alkylated and unalkylated phenols and is preferably a mixture obtained by alkylating until the weight of absorbed alkyl moieties is from 5 to 80% by weight of the original phenols, preferably from 10 to 50% most preferably from 20 to 40%.

As well as the main feedstock added at stage (2) an additional phenol composition may also be added at stage (1). This material may be the same as the feedstock composition or may consist of one or more other phenols which are required to be in the final triaryl phosphate product. Preferably, such an additional composition is not used and in any case, as a general rate, best results are not obtained when more than 1/4, or at most 3/4, mole of such material is present at stage (1) per atom of phosphorus in the phosphorylating agent.

Preferably the recycle composition represents from 1 to 2, most preferably 1 to 1.5 moles of phenol per atom of phosphorus in the phosphorylating agent.

In the first stage of the process the phosphorylating agent is preferably phosphorus oxychloride, POCl₃, but may be any other known agent e.g. phosphorus oxybromide, phosphorus pentoxide, phosphoric acid, phosphorus trichloride or phosphorus pentachloride. The reaction may be conducted according to known techniques, e.g. at a temperature of 15° to 300° C, preferably 100°-280° C, e.g. 200°-280° C and in the presence of catalyst, such as a Lewis acid, e.g. aluminium chloride, or magnesium chloride in conventional quantity, e.g. 0.001 to 5% more usually 0.05 to 1% by weight on the phenol. Other conventional catalyst such as alkyl titanate esters may also be used.

In operation of the novel process the recycle composition will tend to be progressively enriched with the less reactive phenols from the feedstock composition until an equilibrium condition is reached. It will be appreciated that all the phenols of the recycle composition ultimately derive from the feedstock composition and possibly the additional phenol composition, if there is one. To assist in arriving at eqilibrium a purge of phenols may be taken from the recycle composition if desired and may be discarded; distilled to recover fractions suitable for reintroduction into either of the feedstock compositions; chemically converted to other phenols suitable for use in the feedstock compositions e.g. by reaction with phenol itself in the presence of a Friedel Crafts catalyst or otherwise re-used.

The process parameters obtaining at equilibirum recycle conditions will be chosen according to the nature of the feedstock and the desired product, the type of reactor used and process economics but particularly advantageous results are obtained where the recycle composition comprises at least 40 moles %, preferably at least 70 moles %, e.g. at least 80 moles %, or at least 90 moles % of dialkyl and/or polyalkyl phenols having, in each molecule, at least one group of three or more carbon atoms in a position ortho to the phenolic hydroxyl group. The feedstock composition will comprise a minor molar proportion of such phenols.

Especially beneficial appears to be the case where the recycle composition comprises at least 40 moles %, preferably at 60 moles 2,6-di-isopropyl phenol and/or 2,4,6-tri-isopropyl phenol. The feedstock composition will comprise a major molar proportion of such phenols. In some cases the use of at least 80 moles %, or even at least 95 moles % of the 2,6-di-isopropyl phenol and/or 2,4,6-tri-isopropyl phenol may be advantageous.

In the second stage of the process the stage (1) product is reacted with the feedstock phenol composition under conventional conditions for the phosphorylation of alkyl phenols, which may conveniently be the same conditions as in stage (1), to produce a triaryl phosphate product. The term "triaryl phosphate product" herein includes for the sake of convenience the products obtained when phosphorus trichloride or phosphorus pentachloride are used as phosphorylating agents, viz triaryl phosphites and dichlorotriaryl phosphates. Such materials may be respectively oxidised and hydrolysed by known means in a facile manner to give triaryl phosphates proper.

The third and fourth stages of the novel process may be conducted by standard conventional techniques by stripping unreacted phenols from the stage (2) product with subsequent recycle to stage (1) optionally after purging.

The process of the invention may be conducted batchwise or continuously. The batch version at its most rudimentary will comprise simply the consecutive introduction of a recycle composition of phenols, optionally admixed with additional phenol composition, together with phosphorylating agent and catalyst into a heated, stirred reaction vessel and reacting and causing the phosphorylating reaction to occur; (b) introduction of feedstock composition and further reaction to produce triaryl phosphate product; (c) distillation of this product to separate triaryl phosphate product and recycle composition and (d) subsequent reintroduction of recycle composition into the same or a different reaction vessel for repetition of stage (a). However, several variants of this procedure may be devised using two or more reaction vessels each receiving recycle composition from the distillation (c) conducted in the preceding vessel in the series. In the limit, it is possible to perform the process on a semi-continuous basis by this means.

Continuous operation is preferred. According to this embodiment recycle composition phenols, (optionally together with additional phenol composition), phosphorylating agent and catalyst may be fed into an upper part of a vertical reaction vessel wherein stage (1) of the process occurs during descent of the reactants to a lower part of the vessel into which feedstock composition phenols are introduced to initiate stage (2) of the process. The bottoms from the column, comprising triaryl phosphate product and unreacted phenols may continuously or intermittently be fed to a distillation column to separate off the unreacted phenols as the recycle composition for return to the reaction vessel.

It will be appreciated that the relative proportions of the recycle composition of phenols and the feedstock composition is determined by the excess of feedstock composition over that needed for full phosphorylation which is introduced at stage (2) of the process. A high excess will make for a correspondingly high proportion of recycle composition. By adjusting the proportion of feedstock composition and if necessary by taking a purge of recycle composition either continually or intermittently any desired equilibrium condition may be attained.

At the commencement of the reaction there will normally of course be no recycle composition available and to begin operations the feedstock composition may be used in this capacity. Thereafter the process may be allowed to reach equilibrium as described.

Triaryl phosphates may be recovered from the stage (3) product by contacting or reacting the crude product with aqueous alkali to remove acidity and excess phenols, followed if desired by treatment with an oxidising agent to remove the oxidisable impurities. Alternatively, the mixture may be purified by distilling the crude product under reduced pressure to separate a main portion which is contacted or extracted with aqueous alkali and treated, if desired, with an oxidising agent.

The triaryl products made by the novel process preferably comprise from 20 to 85 moles percent of the aryl moieties as aryl groups possessing alkyl substituents having from 3 to 12 carbon atoms, preferably such aryl groups are non-tertiary groups and most preferably they are isopropyl or sec-butyl groups. The remaining aryl moieties are preferably phenyl or alkyl phenyl groups comprising less than two alkyl carbon atoms per molecule but the presence of other types of aryl moieties is not excluded. The most preferred remaining aryl groups are phenyl itself.

Triaryl phosphate products of the invention may be used in a variety of applications, notably as plasticizers for polymeric compositions such as polyolefines, cellulosic esters, polymers and co-polymers of vinyl chloride and vinylidene chloride post-halogenated polyvinyl chloride and post-halogenated polyolefines. The products may also be used as functional fluid e.g. lube oil and hydraulic fluid, additives and as ignition control additives for fuels. A particular use is in the plasticization of vinyl chloride resins in which use it has, surprisingly, been found that unusually high concentrations of 2,6-dialkyl phenyl phosphates contained in the recycle composition do not have the adverse effect on light stability which would have been predicted. Polymeric resin compositions comprising, as plasticizers, a triaryl phosphate mixture produced by the novel process constitutes a further aspect of the invention. Particularly preferred for such use are novel triaryl phosphate mixtures produced by a process as aforesaid wherein the recycle composition comprises at least 40 moles %, molar proportion of 2,6-di-isopropylphenol and the feedstock phenol composition has been prepared by alkylation of a material which consists essentially of phenol itself. Resin compositions comprising a polymer or co-polymer of PVC are preferred. These will normally comprise from 30 to 150 parts by weight, normally 30 to 100 or 40 to 70 parts by weight of the triaryl phosphate plasticizers. They may further comprise other known PVC stabilizers such as conventional phenolic materials and alternative plasticizers to supplement or partially replace the said triaryl phosphates The invention will now be illustrated by reference to the following Examples in which all parts are by weight:

EXAMPLE 1

There was used a reactor consisting of a substantially cylindrical sided vessel, 33 feet high by 18 inches diameter and packed with 15 trays, being plates with 2 bubble caps and 2 downcomers, 1 disengagement Prately plate, 4 plates with a single, central downcomer, 4 plates with 6 small downcomers and 1 plate with 4 large downcomers. Inlets were provided at the top of the reactor for recycle composition phenol and phosphorus oxychloride input and at a point in the side of the reactor one third the distance from the top for feedstock composition phenol input. Outlets at the bottom of the reactor and at a point in the side half way up the reactor from the bottom were provided for the removal of the triaryl phosphate product and hydrogen chloride of reaction respectively.

The reactor was held at a temperature of 200° – 280° C whilst streams of the following compositions circulated through the points noted.

| (1) Recycle composition phenols - rate 5,000 lbs/hr | |
|---|---|
| Phenol | 8.3 |
| o-isopropylphenol | 50.2 |
| m + p isopropylphenol | 0.6 |
| 2,6-di-isopropylphenol | 30.9 |
| 2,4-di-isopropylphenol | 3.9 |
| 2,3 + 2,5-di-isopropylphenol | 0.6 |
| 2,4,6-tri-isopropylphenol plus AlCl₃ Catalyst | 5.5 |
| (2) Feedstock composition phenols - rate 5000 lbs/hr. | |
| Phenol | 32.6 |
| o-isopropylphenol | 31.7 |
| m + p isopropylphenol | 14.9 |

-continued

| | |
|---|---|
| 2,6-di-isopropylphenol | 6.5 |
| 2,4-di-isopropylphenol | 10.4 |
| 2,3 + 2,5-di-isopropylphenol | 2.5 |
| 2,4,6-tri-isopropylphenol plus AlCl₃ Catalyst | 2.1 |
| (3) Phosphorus oxychloride - rate 1,900 lbs/hr. | |
| (4) HCl off gas at 1,350 lbs/hr. | |

Phenols were condensed from the off gas combined with the recycle composition. The bottoms were distilled 250° C and 1 mm psi pressure to recover 6,000 lbs/hr of substantially pure triaryl phosphate and 5,000 lbs/hr of recycle composition phenols. Aluminium catalyst was continuously recycled with sufficient make-up AlCl₃ to maintain concentration of aluminium in the reactor in the range 0.1 to 0.5% by weight.

EXAMPLE 2

A further procedure was carried out in the same manner as in Example 1 save that the recycle composition had the following composition (% by weight)

| | |
|---|---|
| Phenol | 2.4 |
| o-isopropylphenol | 32.1 |
| m + p isopropylphenol | 0.8 |
| 2,6-di-isopropylphenol | 44.8 |
| 2,4-di-isopropylphenol | 4.0 |
| 2,3 + 2,5-di-isopropylphenol | 1.1 |
| 2,4,6-tri-isopropylphenol + AlCl₃ catalyst | 14.5 |
| 2,4,5-tri-isopropylphenol | 0.3 |

In both Examples a triaryl phosphate products were found to be highly suited for use as functional fluid additives and as PVC plasticizers.

We claim:

1. A process of manufacturing triaryl phosphate mixtures which comprises:
    1. reacting a phosphorylating agent selected from the group consisting of phosphorus oxychloride, phosphorus oxybromide, phosphorus pentoxide, phosphoric acid, phosphorus trichloride and phosphorus pentachloride, with a recycle composition of phenols, the total molar proportion of phenols to atoms of phosphorus in the phosphorylating agent being less than 3:1;
    2. reacting the product of stage (1) with a feedstock composition of phenols said feedstock composition comprising phenol, at least one monoalkylphenol, and phenol selected from the group consisting of dialkylphenols and trialkylphenols and being the reaction product obtained by alkylating (i) phenol, or (ii) a mixture of phenols comprising a major molar portion of phenols having less than three alkyl carbon atoms, with (iii) a phenol alkylating agent containing from three to sixteen carbon atoms per molecule, the proportion of feedstock composition added at (2) being such that the molar ratio of the total of phenols fed into the process to phosphorus atoms is at least 3:1 to form a mixture of (a) triaryl phosphates and (b) unreacted phenols which is enriched in said phenol selected from the group consisting of dialkylphenols and trialkylphenols when compared to said feedstock composition;
    3. recovering said unreacted phenols which is enriched in said phenol selected from the group consisting of dialkylphenols and trialkylphenols from the stage (2) product which is then said recycle composition of phenols; and 4. recycling said recycle composition to stage (1).

2. A process according to claim 1 wherein the feedstock composition has been made by alkylating phenol itself with an alkylating agent containing from 3 to 16 carbon atoms per molecule.

3. A process according to claim 2 wherein the feedstock composition has been made by alkylating phenol itself with an alkylating agent containing from 3 to 6 carbon atoms.

4. A process according to claim 3 wherein the alkylating agent is an alkene having from 3 to 6 carbon atoms.

5. A process according to claim 4 wherein the feedstock composition is a mixture obtained by alkylating until the weight of absorbed alkyl moieties is from 5 to 80% by weight of the original phenols.

6. A process according to claim 5 wherein the feedstock composition is a mixture obtained by alkylating until the weight of absorbed alkyl moieties is from 20 to 40% by weight of the original phenols.

7. A process according to claim 1 wherein additional composition feedstock phenols which comprises not more than ¾ moles per mole of phosphorus in the phosphorylating agent is also reacted with said phosphorylating agent in stage (1).

8. A process according to claim 7 wherein the additional composition of feedstock phenols comprises not more than ½moles per atom of phosphorus in the phosphorylating agent.

9. A process according to claim 1 wherein the recycle composition comprises from 1 to 2 moles of phenols per atom of phosphorus in the phosphorylating agent.

10. A process according to claim 9 wherein the recycle composition comprises from 1 to 1.5 moles of phenols per atom of phosphorus in the phosphorylating agent.

11. A process according to claim 1 wherein the recycle composition comprises at least 40 moles percent of phenols selected from the group consisting of dialkylphenols and trialkylphenols having, in each molecule, at least one group of three or more carbon atoms in a position ortho to the phenolic hydroxy group.

12. A process according to claim 11 wherein the recycle composition comprises at least 80 moles percent of said dialkyl and/or polyalkylphenols.

13. A process according to claim 11 wherein the recycle composition comprises at least 40 moles percent of at least one phenol selected from the group consisting of 2,6-di-isopropylphenol and 2,4,6-tri-isopropylphenol.

14. A process according to claim 13 wherein the recycle composition comprises at least 60 moles percent of said phenol (s).

15. A process according to claim 1 which comprises consecutively:

a. introduction of the recycle composition of phenols, together with a phosphorylating agent and catalyst into a heated, stirred reaction vessel and causing the phosphorylation reaction to occur.

b. introduction into the vessel of the feedstock composition and causing further reaction to take place c. distillation of the product of step (b) thereby recovering a triaryl phosphate product and recycle composition of phenols d. subsequent reintroduction of the recycle composition of phenols obtained in stop (c) into the same or different vessel and repetition of step (a).

16. A process according to claim 1 which comprises continuously feeding recycle composition of phenols, and phosphorylating agent into an upper part of a vertical reaction vessel; continuously feeding feedstock composition to a lower part of said vessel; recovering a mixture of unreacted phenols and triaryl phosphate product from a bottom part of said vessel; and continuously or intermittently recovering said unreacted phenols and recycling them to form the recycle composition to said upper part of the vessel.

17. A process according to claim 15 wherein the recycle composition of phenols is admixed with additional feedstock composition.

18. A process according to claim 16 wherein the recycle composition of phenols is admixed with additional feedstock composition.

19. A process according to claim 1 wherein the phosphorylating agent is phosphorus oxychloride.

20. A process according to claim 11 wherein said phenol alkylating agent is selected from the group consisting of alkyl halides, alkanols, and alkenes; wherein the total molar proportion of phenols to atoms of phosphorus in the phosphorylating agent in the reaction stage (1) is from one to two moles of phenols per atom of phosphorus in the said phosphorylating agent; and wherein the total amount of phenols in the reaction stage (2) is in excess of three moles of phenols per atom of phosphorus.

21. A process according to claim 20 wherein said phenol alkylating agent is an alkene having from three to six carbon atoms; wherein said feedstock composition of phenols is obtained by alkylating phenol; and wherein said feedstock composition of phenols is a mixture obtained by alkylating phenol until the weight of absorbed alkyl moieties is from 20 to 40% by weight of the original phenol.

22. A process according to claim 21 wherein said feedstock composition of phenols consists essentially of isopropylphenols; and wherein said recycle composition comprises at least 60 mole percent of at least of one phenol selected from the group consisting of 2,6-di-isopropylphenol and 2,4,6-tri-isopropylphenol.

23. A process according to claim 22 wherein said fhe phosphorylating agent is phosphorus oxychloride.

24. A process according to claim 1 wherein said phenol alkylating agent is selected from the group consisting of alkyl halides, alkanols, and alkenes.

* * * * *